United States Patent [19]

Heck

[11] 4,428,960
[45] Jan. 31, 1984

[54] 3-AMINO-6-SUBSTITUTED THIO-1-AZABICYCLO(3.2.0)HEPT-6-EN-2-ONE-7-CARBOXYLIC ACIDS

[75] Inventor: James V. Heck, Fanwood, N.J.

[73] Assignee: Merck & Co., Inc., Rahway, N.J.

[21] Appl. No.: 369,954

[22] Filed: Apr. 19, 1982

[51] Int. Cl.³ ............... C07D 205/12; A61K 31/395
[52] U.S. Cl. .................. 424/274; 260/245.2 R; 424/244; 424/263; 424/272; 424/250; 424/251; 424/273 R; 424/270; 548/515
[58] Field of Search .......... 360/245.2 R, 245.2 T; 424/273 R, 244, 272, 246, 274, 263, 270, 250, 251; 548/515

[56] References Cited
U.S. PATENT DOCUMENTS 4,372,965 2/1983 Christensen et al. ........ 260/245.2 T Primary Examiner—Nicholas S. Rizzo
Attorney, Agent, or Firm—Hesna J. Pfeiffer; Paul H. Ginsburg

[57] ABSTRACT

Disclosed are 3-amido-6-substituted thio-1-azabicyclo[3.2.0]hept-6-en-2-one-7-carboxylic acids (I) and their pharmaceutically acceptable salts and esters which are useful as antibiotics

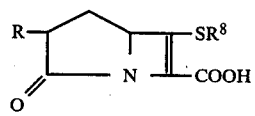

wherein: R is $NH_2$, $R^1$ NH, $R^1$ is acyl; and $R^8$ is inter alia, unsubstituted and substituted alkyl, alkenyl, aryl, and aralkyl.

Also disclosed are processes for the preparation of such compounds; pharmaceutical compositions comprising such compounds; and methods of treatment comprising administering such compounds and compositions when an antibiotic effect is indicated.

4 Claims, No Drawings

3-AMINO-6-SUBSTITUTED THIO-1-AZABICYCLO(3.2.0)HEPT-6-EN-2-ONE-7-CARBOXYLIC ACIDS

BACKGROUND OF THE INVENTION

This invention relates to 3-amido-6-substituted thio-1-azabicyclo[3.2.0]hept-6-en-2-one-7-carboxylic acids (I) and the pharmaceutically acceptable salt and ester derivatives thereof which are useful as antibiotics:

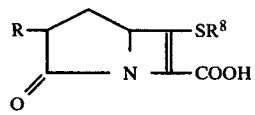

wherein: R is $R^1NH$; wherein $R^1$ is hydrogen or an acyl radical known to be effective in the related bicyclic β-lactam antibiotic art, such as, the penicillins, cephalosporins, and 6-amido penems and carbapenems. $R^8$ is, inter alia, unsubstituted and substituted alkyl, alkenyl, aryl, and aralkyl. The 6-substituent $R^8$ is defined in greater detail below. Also, for the purpose of defining $R^8$, European Pat. Appln. No. 80102076.9 (filed Apr. 18, 1980) is incorporated herein by reference. The cited document discloses certain 1-carbadethiapenem antibiotics bearing a 2-$SR^8$ side chain; it is the very definition of that side chain (—$SR^8$, or —$R^8$) which is incorporated herein by reference. To the extent that the following U.S. patents define $R^1$ as acyl, they are hereby incorporated herein by reference: U.S. Pat. No. 4,217,453 (issued Aug. 12, 1980); U.S. Pat. No. 4,226,866 (issued Oct. 7, 1980).

This invention also relates to the carboxyl derivatives of I which are antibiotics and which may be represented by the following generic structure (I):

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both Gram positive bacteria such as *S. aureus*, *Strep. pyogenes*, and *B. subtilis*, and Gram negative bacteria such as *E. coli*, *Pseudomonas*, *Proteus morganii*, *Serratia*, and *Klebsiella*. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently be summarized by the following reaction diagram:

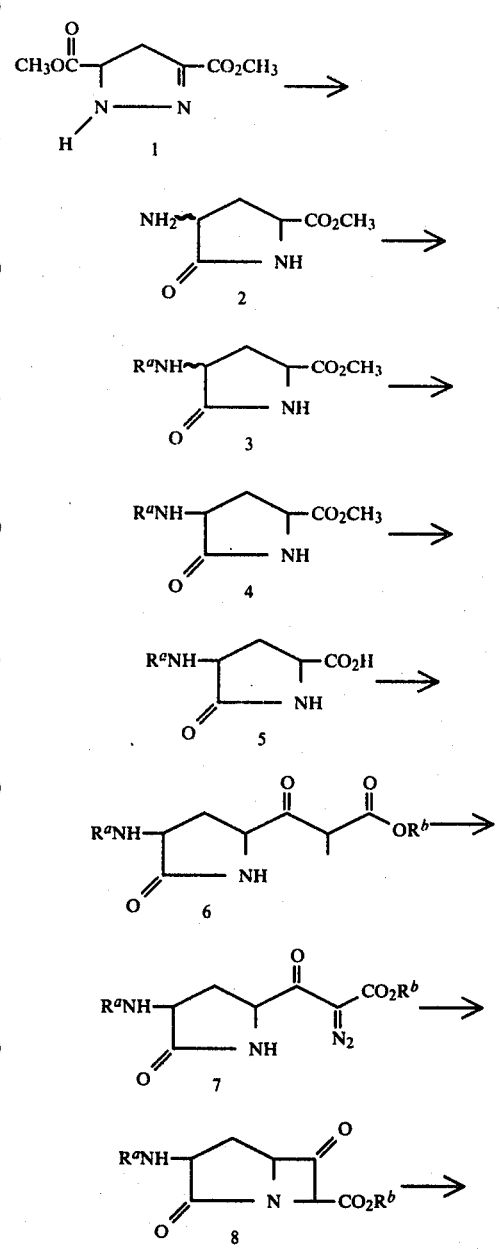

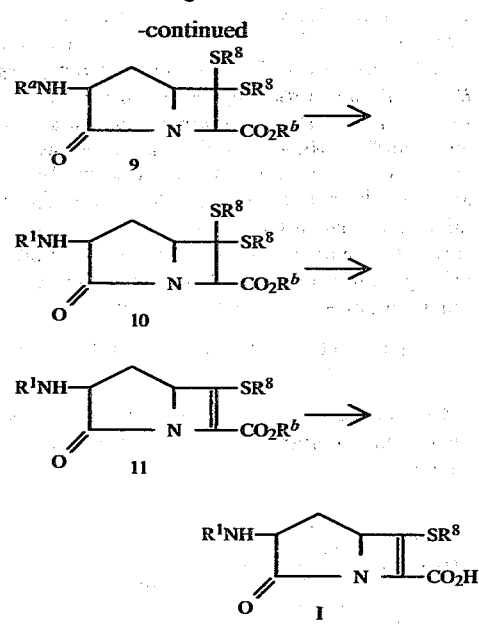

In words relative to the above diagram, the transformation 1 to 2 is accomplished by treating the pyrazoline starting material 1, in a solvent such as ethanol-tetrahydrofuran, methanol-tetrahydrofuran, or the like, with hydrogen at a pressure of from 150 to 300 atmospheres in the presence of a catalyst such as Raney nickel, platinum, palladium, or the like, at a temperature of from 80° to 120° C. for from 6 to 12 hours.

The transformation 2 to 3 is accomplished by treating 2, in a solvent such as dichloromethane, chloroform, tetrahydrofuran, or the like, in the presence of base such as triethylamine, diisopropylethylamine, pyridine, or the like, with a reagent calculated to establish $R^a$, wherein $R^a$ is alkyl, aryl, or aralkyl, such as trityl, 4,4'-dimethoxytrityl, p-anisyldiphenylmethyl, benzhydryl, or the like. Typically the $R^a$ reagent is for example: trityl chloride, 4,4'dimethoxytrityl, p-anisyldiphenylmethylchloride, benzhydrylchloride, or the like.

The pyrrolidinone intermediate 3 may be separated into its component isomers. The cis isomer (4) is preferred, and typically separation is accomplished by crystallization and chromatography; for example 3 ($R^a$=trityl) is dissolved in dichloromethane from which the trans-isomer selectively crystallizes. Chromatography of the mother liquors over silica gel with dichloromethane-methanol mixtures affords the pure cis isomer 4.

The carboxyl de-protection transformation, 4 to 5 is accomplished by hydrolysis. Typically, 4 in a solvent such as methanol, ethanol, tetrahydrofuran, or the like, is treated with 1.0 equivalent of aqueous alkali metal hydroxide (e.g. KOH, NaOH) at from 0° to room temperature for 2 to 4 hours, followed by neutralization and extractive workup.

The addition 5 to 6 is accomplished by treating 5 with 1,1'-carbonyldiimidazole, or the like, in a solvent such as tetrahydrofuran, dimethoxyethane, or the like, at a temperature of from 0° to 50° C., followed by the addition of 1.1 to 3.0 equivalents of ($R^6O_2CCH_2CO_2$) Mg, at a temperature of from 0° to 50° C. for from 1 to 48 hours; $R^b$ is a readily removable carboxyl protecting group such as p-nitrobenzyl, benzyl, or the like.

The diazo species 7 is prepared from 6 by treating 6 in a solvent such as $CH_3CN$, $CH_2Cl_2$, THF, or the like, with an azide such as p-carboxybenzene sulfonylazide, toluenesulfonylazide, methanesulfonylazide, or the like, in the presence of a base such as triethylamine, pyridine, $(C_2H_5)_2NH$, or the like, for from 1 to 50 hours at 0°–25° C.

Cyclization (7 to 8) is accomplished by treating 7 in a solvent such as benzene, toluene, dichloromethane, THF, or the like, at a temperature of from 50°–100° C. for from 1–5 hours in the presence of a catalyst such as bis (acetylacetonato)Cu(II) [Cu(acac)$_2$], CuSO$_4$, Cu powder, Rh(OAc)$_2$ or Pd(OAC)$_2$. Alternatively, the cyclization may be accomplished by irradiating 7 through a pyrex filter (a wave length greater than 300 nm) in a solvent such as benzene, CCl$_4$, diethylether, or the like, at a temperature of from 0°–25° C. for from 0.5 to 2 hours. ["OAc"=acetate.]

The transformation 8 to 9 is accomplished by treating 8, in a solvent such as acetonitrile, tetrahydrofuran, mixtures of the above, or the like, with 1.0 to 1.1 equivalents of a strong base such as 1,8-Diazabicyclo[5.4.0]undec-7-ene (DBU), 1,5-Diazabicyclo[4.3.0]non-5-ene, or the like, in the presence of (OO)$_2$POCl, p-toluenesulfonylchloride, trifluoromethanesulfonylchloride (O=phenyl), followed by treating with 2.0 eq. of the reagent $R^8SH$ in the presence of 2.0 to 2.5 equivalents of a base, such as, diisopropylethyl amine, triethylamine, or the like. $R^8$ is as defined above. Representative values of $R^8$, expressed in the form of the reagent HSR$^8$, are given below.

The N-acylation reaction to establish $R^1$ is conveniently performed on intermediate 9. The nitrogen protecting group $R^a$ may be conveniently removed by treatment of 9 with 1.0 equivalent of a mineral acid, such as hydrochloric acid, sulfuric acid, or the like, in an alcohol solvent such as methanol or ethanol at 0° to room temperature for 0.5 to 2 hours. The primary amine corresponding to 9 where $R^a$=H may be isolated as a free base or salt and then acylated by procedures analogous to those employed for 6-aminopenicillanic acid esters or 7-amino cephalosporanic acid esters. For example, the amine 9 ($R^a$=H) is treated with an acid chloride of choice designed to provide $R^1$ in the presence of triethylamine, pyridine or the like, in dichloromethane, chloroform, tetrahydrofuran, or the like, at from 0° to room temperature for from 0.5 to 4 hours, resulting in the formation of acyl derivative 10.

The acyl group $R^1$ is as described above. Representative values for $R^1$, and suitable acylating agents to establish $R^1$, are given below.

Conversion of 10 to 11 may be effected by a combination of oxidation and elimination. For example, treatment of 10 with 1.0 equivalent of an oxidizing agent such as m-chloroperbenzoic acid, peracetic acid, or the like, in a solvent such as dichloromethane, chloroform, or the like, at −20° to 0° for from 0.5 to 2 hours affords a mixture of diastereomeric monosulfoxides which need not be separated. Direct treatment of the crude sulfoxide mixture with a strong amine base such as 1,8-diazabicyclo[5.4.0]undec-7-ene (DBU), 1,5-diazabicyclo[4.3.0]non-5-ene, tetramethylquanidine, or the like, in a solvent such as dichloromethane, chloroform or tetrahydrofuran at 0° to 50° for from 1 to 3 hours affords the olefin 11 after chromatographic isolation.

The final deblocking step 11 to I is accomplished by conventional procedures such as hydrolysis or hydrogenation. Typically 11 in a solvent such as dioxane-water-ethanol, tetrahydrofuran-aqueous dipotassium hydrogen phosphate-isopropanol, or the like, is treated under a hydrogen pressure of from 1 to 4 atmospheres in the presence of a hydrogenation catalyst such as palladium on charcoal, palladium hydroxide, or the like, at a temperature of from 0° to 50° C. for from 0.5 to 4 hours to provide I.

In further explanation of the N-acylation reaction 9 to 10, it was noted above that the transformation may be accomplished by any of a variety of well known procedures (the analogous reactions in the 6-amido penicillin and 7-amido cephalosporin series are well known and are apposite here) such as treating 9 in a solvent such as methylene chloride, chloroform, or the like, with an acid chloride calculated to provide the acyl radical $R^1$ in the presence of from 1–5 equivalents of $K_2HPO_4$ in water, or in the presence of pyridine at a temperature of from 0°–25° C. for from 5–60 minutes. Preferred acyl groups $R^1$ and representative acylating agents are given below:

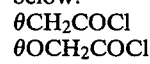
θCH$_2$COCl
θOCH$_2$COCl

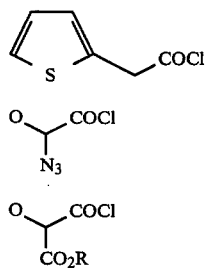

IDENTIFICATION OF THE ACYL RADICAL $R^1$ OF STRUCTURE I

In the generic representation of the compounds of the present invention (I, above), the acyl radical represented by $R^1$ can, inter alia, be substituted or unsubstituted: aliphatic, aromatic or heterocyclic, araliphatic or heterocyclylaliphatic carboxylic acid radical, a substituted or unsubstituted: carbamyl radical or a carbothioic acid radical. One group of acyl radicals can be represented by the general formula:

wherein X is O or S and R″ represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O, N and S; such above-listed groups can be unsubstituted or can be substituted by radicals such as OH, SH, SR° (R° is lower alkyl or aryl such as phenyl), alkyl or alkoxy groups having 1 to about 6 carbon atoms, halo such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β, β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, 1-phenylphenyl, p-aminoethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-thienylmethyl, 3-thienylmethyl, tetrazolylmethyl benzamidinomethyl and cyclohexylamidinomethyl.

The acyl group can also be a radical of the formula:

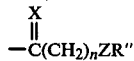

wherein X is O or S and n is 0–4, Z represents oxygen, sulfur, carbonyl or nitrogen and R″ is defined as above. Representative members of the substituent

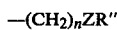

that might be mentioned are allylthiomethyl, phenylthiomethyl, butylmercaptomethyl, α-chlorocrotylmercaptomethyl, phenoxymethyl, pehnoxyethyl, phenoxybutyl, phenoxybenzyl, diphenoxymethyl, dimethylmethoxymethyl, dimethylbutoxymethyl, dimethylphenoxymethyl, 4-tuanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)-phenoxymethyl, p-(carboxymethyl)-phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

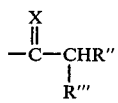

wherein R'' is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent:

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(-)-α-hydroxybenzyl, α-carboxybenzyl, α-amino(3-thienyl)-methyl D-(-)-α-amino-3-chloro-4-hydroxybenzyl, α-amino(cyclohexyl)methyl, α-(5-tetrazolyl)-benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(-)-2-thienyl-guanidinomethyl, D-(-)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl-)aminomethyl, 2-(5-chlorothienyl)-hydroxymethyl, 2-(5-chlorothienyl)-carboxy-methyl, 3-(1,2-thiazolyl)aminomethyl, 3-(1,2-thiazolyl)-hydroxymethyl, 3-(1,2-thiazolyl)-carboxymethyl, 2-(1,4-thiazolyl)aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl containing one or more oxygen, sulfur or nitrogen atoms in the ring, such as furyl, quinoxyalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1-6 carbon atoms, heterocyclic or substituted heterocyclic thio groups; or cyano. The substituents on the moieties, $R^3$ and $R^4$, can be halo, carboxymethyl, quanidino, guanidinomethyl, carboxamidomethyl, aminoethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)-acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, aphosphonophenylacetyl, α-amino cyclohexadienylacetyl, α-sulfaminophenylacetyl, α-hydroxyphenylacetyl, α-tetrazolylphenylacetyl and α-sulfophenylacetyl.

Acyls ($R^1$, Structure I) of the following definition are also preferred:

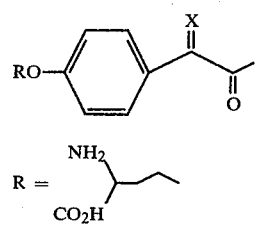

X=O, NOR$^9$; R$^9$=H, alkyl having 1-6 carbon atoms.

$R^1$ of Structure I may also be a readily removable protecting group; a particularly preferred acyl for this purpose is o or p-nitrobenzyloxycarbonyl.

As noted above, the compounds of the present invention may also generally be represented by the following structural formula:

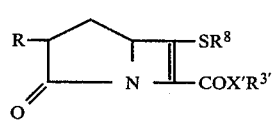

wherein X' is oxygen, sulfur or NR' (R' is hydrogen or loweralkyl having from 1 to 6 carbon atoms); and R$^{3'}$ is hydrogen, or, inter alia, is representatively selected to provide the pharmaceutically acceptable salt, ester, anhydride (R³' is acyl), and amide moieties known in the bicyclic β-lactam antibiotic art; R³' may also be a readily removable blocking group.

IDENTIFICATION OF THE RADICAL —COX'R3'

In the generic representation of the compounds of the present invention (I, above the radical represented by —COX'R³' is hydrogen) and all radicals known to be effective as pharmaceutically acceptable ester, anhydride (R³' is acyl) and amide radicals in the bicyclic β-lactam antibiotic art, such as the cephalosporins and penicillins and nuclear analogues thereof.

Suitable, but representative, blocking esters R³' (X=O) include those selected from the following list which is representative:

(i) R³'=CR$^a$R$^b$R$^c$ wherein at least one of R$^a$, R$^b$, and R$^c$ is an electrondonor, e.g., p-methoxyphenyl. The remaining R$^a$, R$^b$ and R$^c$ groups may be hydrogen or organic substituting groups. Suitable ester groups of this type include p-methoxybenzyloxycarbonyl.

(ii) R³'=CR$^a$R$^b$R$^c$ wherein at least one of R$^a$, R$^b$ and R$^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R³'=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: R$_3^4$SiX' wherein X' is a halogen such as chloro or bromo and R⁴ is alkyl, having 1-6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxmethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R³' radicals of the present invention are those wherein (relative to Structure I above), X' is oxygen and R³' is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

IDENTIFICATION OF R⁸, HSR⁸

R⁸ is independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl, wherein the heteroatom or atoms are selected from O, S, N; wherein the substitutent or substituents relative to the above-named radical values for R⁶, R⁷ and R⁸ are selected from the group consisting of:

—X° halo (chloro, bromo, fluoro)

—OH hydroxy

—OR¹ alkoxy, aryloxy $$-O\overset{O}{\overset{\|}{C}}NR^1R^2 \text{ carbamoyloxy}$$

$$-\overset{O}{\overset{\|}{C}}NR^1R^2 \text{ carbamoyl}$$

—NR¹R² amino $$-N-R^1-\overset{R^2}{\overset{|}{C}}=NR^1 \text{ amidino}$$

$$-N-R^1-\overset{NR^1R^2}{\overset{|}{C}}=NR^1 \text{ guanidino}$$

—SO₂NR¹R² sulfamoyl $$-NH\overset{O}{\overset{\|}{C}}NR^1R^2 \text{ ureido}$$

$$NR^1\overset{O}{\overset{\|}{C}}R^2 \text{ amido}$$

—CO₂H carboxy

—OSO₃R¹ sulphate

—NO₂ nitro

—N⁺(R¹)₃ ammonium (R¹ groups independently chosen)

-continued

—C=NOR² oximino

—CO₂R¹ carboxylate

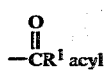
—CR¹ acyl

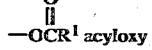
—OCR¹ acyloxy

—SH mercapto

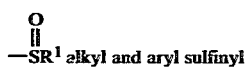
—SR¹ alkyl and aryl sulfinyl

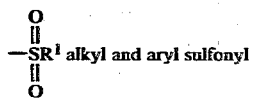
—SR¹ alkyl and aryl sulfonyl

—CN cyano

—N₃ azido

—SR¹ alkyl- and arylthio

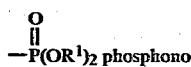
—P(OR¹)₂ phosphono

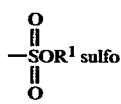
—SOR¹ sulfo

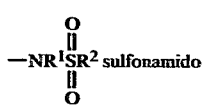
—NR¹SR² sulfonamido wherein, relative to the above listed substituents on $R^6$, $R^7$, and $R^8$, the groups $R^1$ and $R^2$ are independently selected from: hydrogen, alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroalkyl, heteroaralkyl, heterocyclyl and heterocyclylalkyl and wherein the hetero atom or atoms in the above-named heterocyclic moieties are selected from the group consisting of 1–4 oxygen, nitrogen or sulphur atoms and wherein the alkyl moieties associated with said heterocyclic moieties have 1–6 carbon atoms.

Further, relative to $R^8$, radicals which carry an amino group (—NH₂) or an N-substituted amino group (—NR¹H), and which can be represented conveniently as: —R⁸—NH₂, and —R⁸—NR¹H, respectively, there exists the following groups classed under previously defined $R^8$:

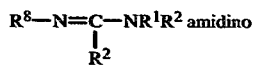
R⁸—N=C—NR¹R² amidino

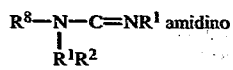
R⁸—N—C=NR¹ amidino

-continued

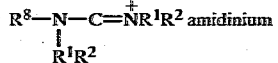
R⁸—N—C=ṄR¹R² amidinium

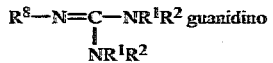
R⁸—N=C—NR¹R² guanidino

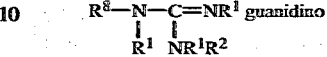
R⁸—N—C=NR¹ guanidino

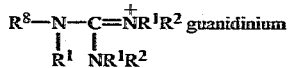
R⁸—N—C=ṄR¹R² guanidinium

HSR⁸ REAGENTS

Relative to the foregoing description of the invention, suitable reagents, HSR⁸, which are utilized in the transformation 8 to 11 are listed below. The list is arranged according to structural and functional characteristics of this side chain —SR⁸; anotation is provided where necessary. It should be noted that only HSR⁸ reagents are expressly shown. The thia side chain of choice —SR⁸ is derived from the corresponding mercaptan reagent HSR⁸, and thus the following list serves to further, specifically disclose —SR⁸ side chains of I which are of special interest. When the mercaptan contains a functional group which might interfere with the intended course of reaction, the offending group is covered. For example, when a basic nitrogen group is encountered (—NHR or —NH₂, for example) it is usually protected by acylation (e.g., —CO₂PNB) and when a carboxyl group (—CO₂H) is present, it is usually protected by esterification (e.g., PNB ester). Such protection also facilitates in the purification of products by chromatographic means. (PNB is p-nitrobenzyl). Such protection is, however, not a necessary requirement for introduction of the —SR⁸ side chain.

It is recognized that SR⁸ side chains in which the R⁸ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved —SR⁸ side chains.

1. Aliphatic Mercaptans: HSR⁸ wherein R⁸ is 1–10 carbon alkyl, cycloalkyl, alkenyl, cycloalkenyl, or alkynyl; R⁸ may be branched or unbranched.

EXAMPLES

HSCH₃
HSCH₂CH₃
HSCH₂CH₂CH₃
HSCH(CH₃)₂
HS(CH₂)₃CH₃

HS—CH—CH₂CH₃
     |
    CH₃

-continued

HSCH₂CH(CH₃)₂

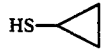

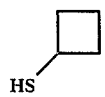

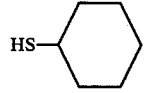

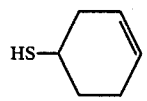

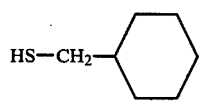

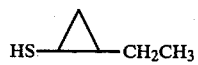

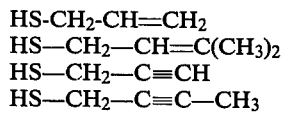

HS—CH₂—CH=CH₂
HS—CH₂—CH=C(CH₃)₂
HS—CH₂—C≡CH
HS—CH₂—C≡C—CH₃

2. Substituted Aliphatic Mercaptans: $HSR^8$ wherein $R^8$ is a 1-10 carbon branched or unbranched alkyl, cycloalkyl, alkenyl, cycloalkenyl, or alkynyl group substituted by one or more halo, OH, $OR^1$,

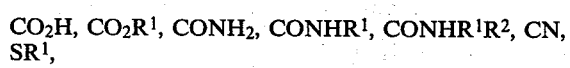

$NH_2$, $NHR^1$, $NR^1R^2$,

$CO_2H$, $CO_2R^1$, $CONH_2$, $CONHR^1$, $CONHR^1R^2$, CN, $SR^1$,

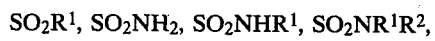

$SO_2R^1$, $SO_2NH_2$, $SO_2NHR^1$, $SO_2NR^1R^2$,

wherein $R^1$ and $R^2$ are as previously defined relative to substituents on $R^8$. Preferred substituents are basic nitrogen-containing groups.

EXAMPLES

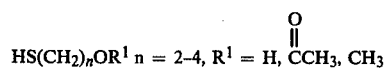

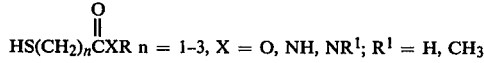

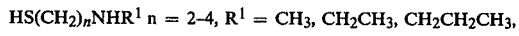

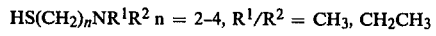

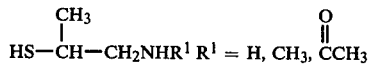

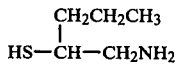

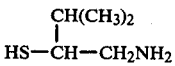

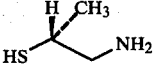

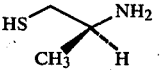

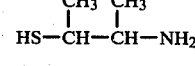

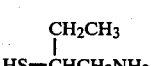

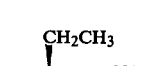

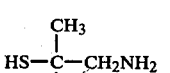

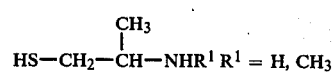

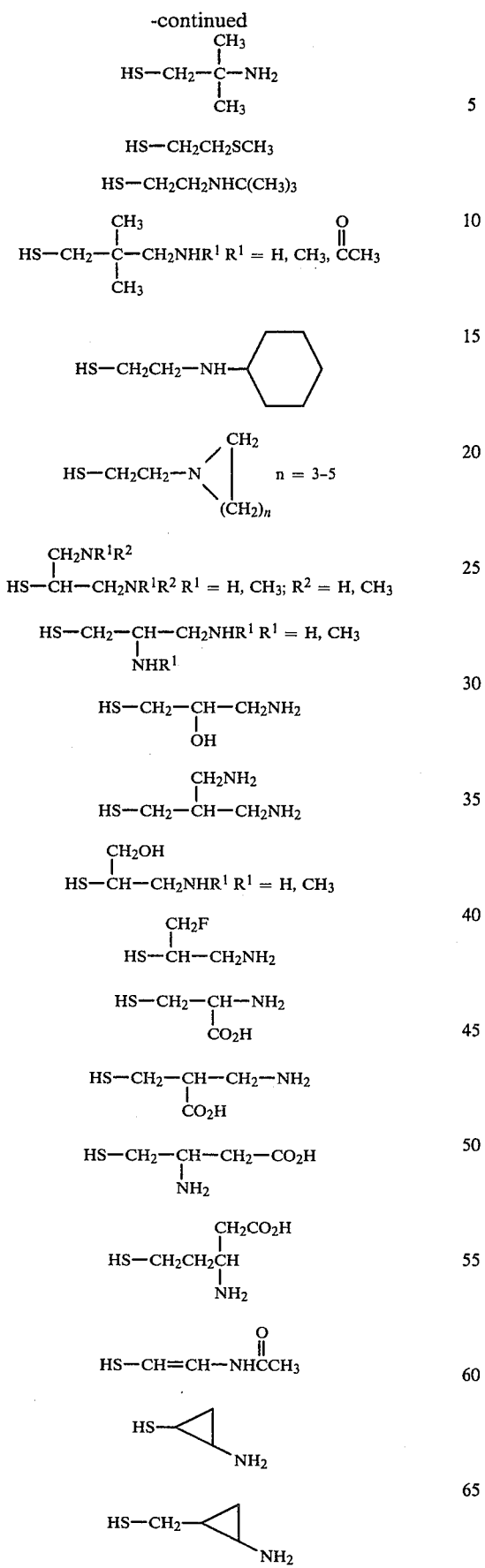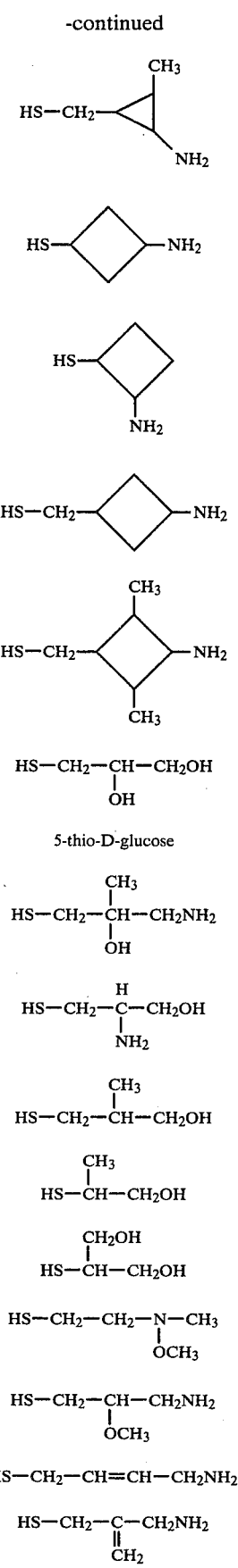

-continued

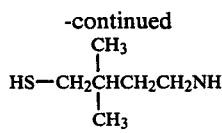

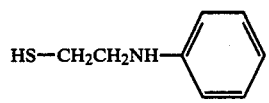

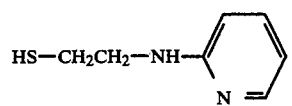

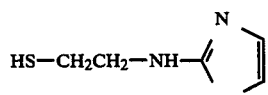

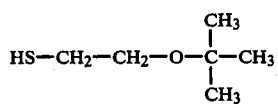

3. Aryl Mercaptans: $HSR^8$ wherein $R^8$ is phenyl or substituted phenyl. The substituents are independently selected from those previously defined for $R^8$. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

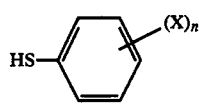

n=1, 2 or 3, X=F, Cl, Br, OH, OR,

$NH_2$, $NHR^1$, $NR^1R^2$, $CH_2NH_2$, $CH_2NR^1R^2$, $CO_2H$, $CO_2R^1$, $COR^1$, $CONH_2$, $CONR^1R^2$, $R^1CONH$, $R^1NHCONH$, $SR^1$,

$SO_2R^1$, $CH_3$, $CF_3$; $R^1$ and $R^2$ are as previously defined under $R^8$.

EXAMPLES

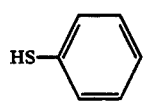 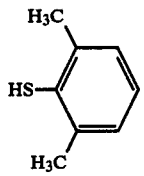

-continued

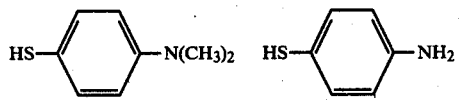

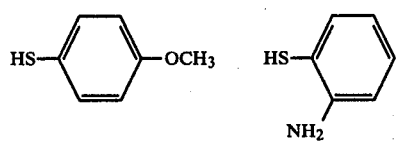

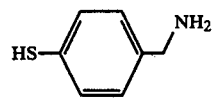

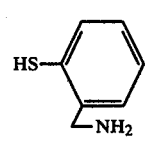

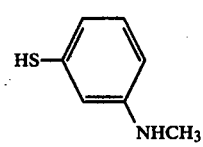

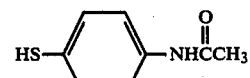

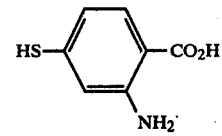

4. Heteroaryl Mercaptans: $HSR^8$ wherein $R^8$ is a substituted or unsubstituted heteroaryl group containing 1-4 O, N or S atoms. Typical substituents include those mentioned above under "Aryl Mercaptans".

EXAMPLES

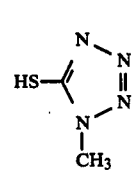 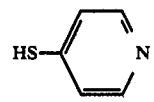

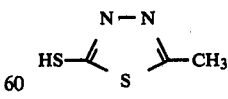 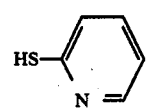

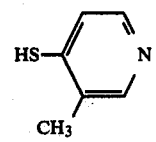

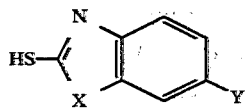
-continued   X = N,  OY = H
             X = S   Y = H, Cl, OCH₂CH₃

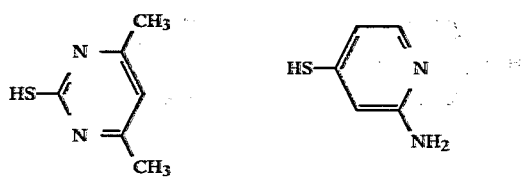

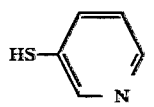

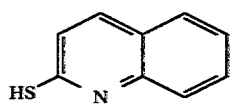

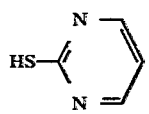

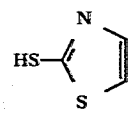

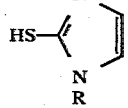

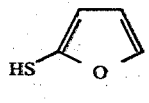   R = H, CH₃

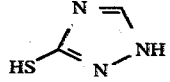

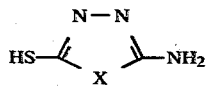

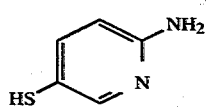   X = NH, S

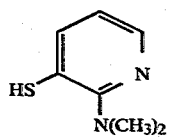

tuted phenyl group. Typical phenyl substituents include those mentioned under "Aryl Mercaptans".

EXAMPLES

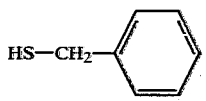

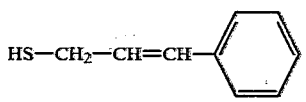

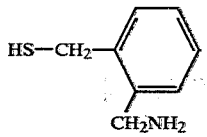

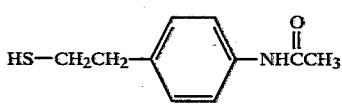

6. Heteroarylaliphatic and Heterocyclylaliphatic, and heterocyclic Mercaptans: HSR⁸ wherein R⁸ is a 1–6 carbon branched or unbranched alkyl, cycloalkyl, alkenyl, or alkynyl group substituted by a heteroaryl or heterocyclyl group containing 1–4, O, N, or S atoms. The heteroaryl or heterocyclic group is unsubstituted or substituted by those substituents mentioned under "Aryl Mercaptans", (No. 3 above).

EXAMPLES

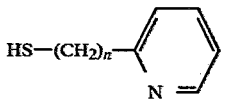

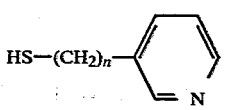

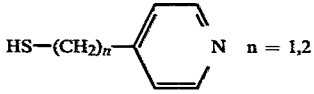   n = 1,2

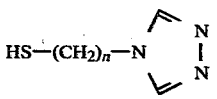

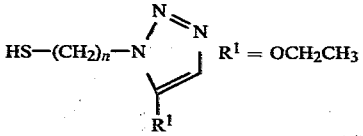   R¹ = OCH₂CH₃

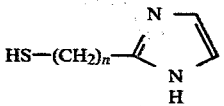

5. Arylaliphatic Mercaptans: HSR⁸ where R⁸ is a 1–6 carbon branched or unbranched alkyl, cycloalkyl, alkenyl, or alkynyl groups substituted by a phenyl or substi- -continued

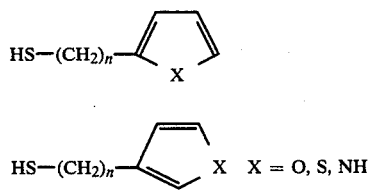

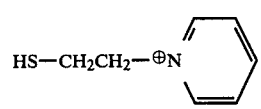 X = O, S, NH

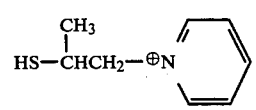

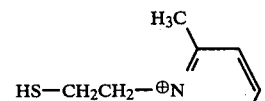

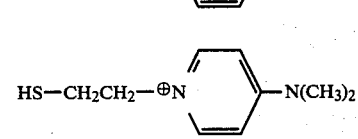

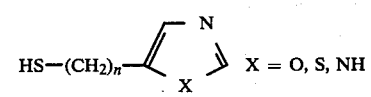

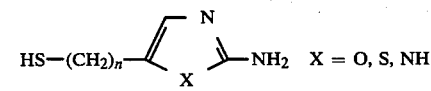 X = O, S, NH

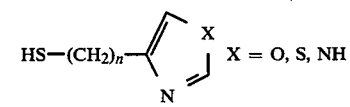 X = O, S, NH

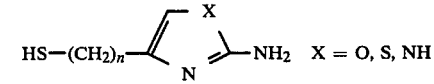 X = O, S, NH

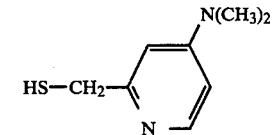

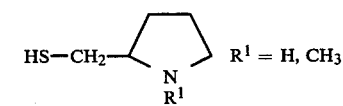 $R^1$ = H, CH$_3$

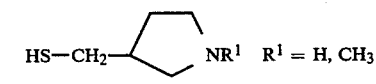 $R^1$ = H, CH$_3$

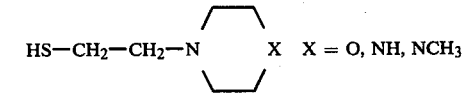 X = O, NH, NCH$_3$

-continued

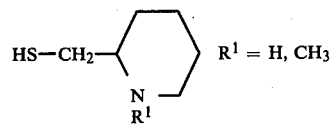 $R^1$ = H, CH$_3$

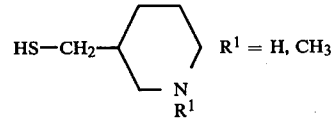 $R^1$ = H, CH$_3$

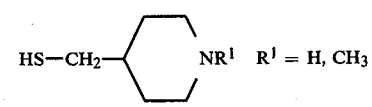 $R^1$ = H, CH$_3$

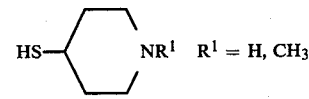 $R^1$ = H, CH$_3$

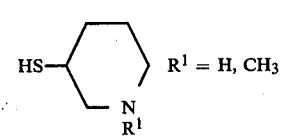 $R^1$ = H, CH$_3$

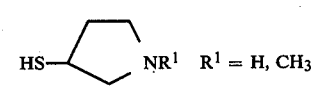 $R^1$ = H, CH$_3$

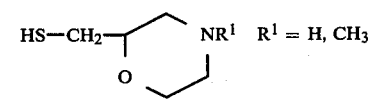 $R^1$ = H, CH$_3$

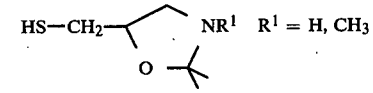 $R^1$ = H, CH$_3$

7 Alkyl-Heteroatom-Alkyl Mercaptans, HSR$^8$: wherein R$^8$ is

—(CH$_2$)$_n$X(CH$_2$)$_m$R$^9$ wherein n=2 to 4, m=2 to 4; X is NR°, O or S; and wherein R° is H, CH$_3$, CH$_2$CH$_3$, CH$_2$CH$_2$OH, or CH$_2$CH$_2$NH$_2$ and R$^9$ is OH, NH$_2$, NHCH$_3$, N(CH$_3$)$_2$,

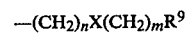

Note, in the above representation, the methylene carbons may be branched; for example:

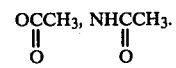

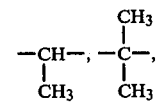

and the like.
The following HSR$^8$ are representative of this class:

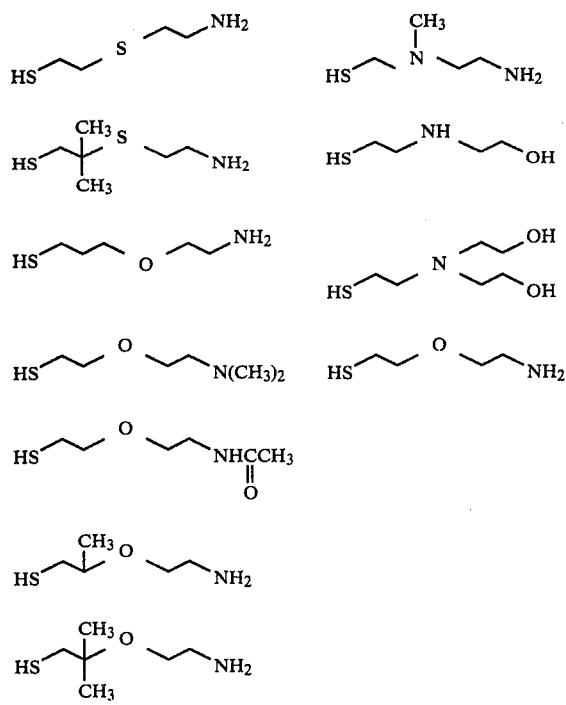

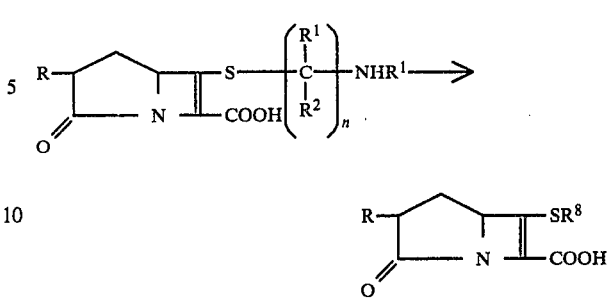

wherein: R⁸ is defined above in this category No. 8.

Relative to the amidino embodiments characterized under this heading, representatively preferred values for $R^1$ and $R^2$ attached to the carbon atom include:
H,
$CH_3$,
$CH_2CH_3$,
$CH_2OH$,
$OCH_3$,
$CH_2NH_2$,
F,
phenyl,
$CF_3$,
$CH(CH_3)_2$,
$CH_2CH_2CH_3$,
$CH_2F$
benzyl, $SCH_3$, $N(CH_3)_2$, $N^+(CH_3)_3X^-$ ($X^-$ defined above)

Representatively preferred values for $R^1$ and $R^2$ attached to the nitrogen atoms include:
H, phenyl, $CH(CH_3)_2$, $C(CH_3)_3$, $NH_2$,
$CH_3$, $NHCH_3$, $N(CH_3)_2$,
$CH_2CH_3$,
$CH_2CH_2OH$,
—$(CH_2)_4$—,
—$CH_2CH_2$—O—$CH_2CH_2$,
$OCH_3$ Representatively preferred values for $R^2$ attached to the imino carbon atom include:
H,
$CH_3$,
$CH_2CH_3$,
phenyl The following values for $HSR^8$ are also classified under the amidino mercaptans, giving rise to amidino embodiments of I:
$R^8$ is:

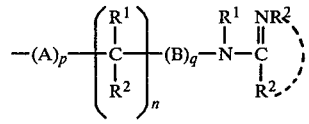

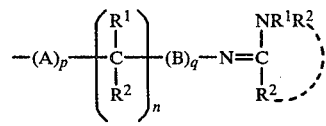

8. Amidino and Amidinium Mercaptans $HSR^8$: wherein $R^8$ is:

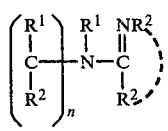

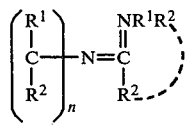

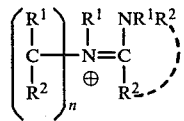

and wherein n=2–6; $R^1$ and $R^2$ are as initially defined under $R^8$, and the dotted line indicates provision for the ring formed by the joinder of substituents carried by the imino carbon atoms. Such amidino and amidinium embodiments of final products I are also conveniently obtained by N-derivatization of the corresponding amino embodiment I according to the procedure disclosed in U.S. Pat. No. 4,194,047 which patent is incorporated herein by reference since the N-derivatization of thienamycin disclosed in the incorporated by reference patent is strictly analogous to the N-derivatization contemplated to achieve the amidino embodiments characterized herein.

The following reaction summarizes such N-derivatization:

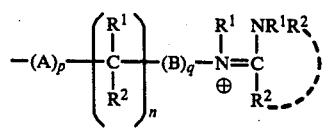

wherein $R^1$, $R^2$ and n are as defined immediately above; p and q are 0 or 1; A and B are selected from: the aforementioned values for $R^8$ expressed in bivalent form ($-R^8-$) from categories No.'s 1–7; thus, A and B (or ($-R^8-$) are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); aryl aliphatic (see Class No. 5, above); heteroarylaliphatic, heterocyclylaliphatic, and heterocyclic (see Class No. 6, above); and alkylheteroatom-alkyl (see Class No. 7, above); and B can also be selected from —O— and —$NR^1$—.

EXAMPLES

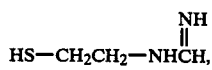
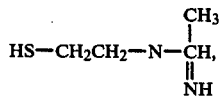
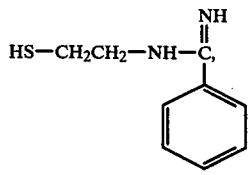
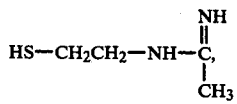
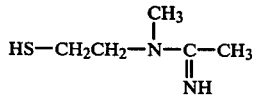
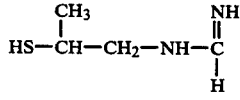
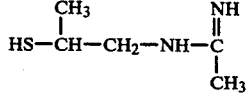
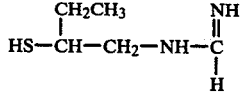
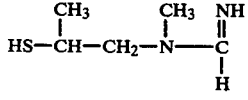

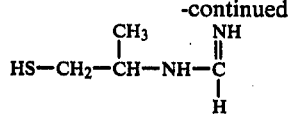
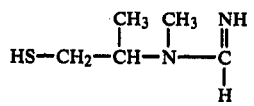
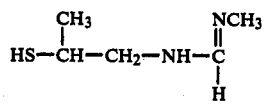
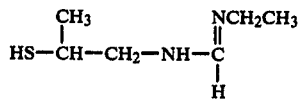
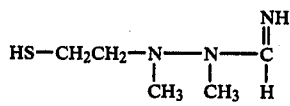
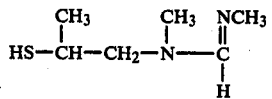
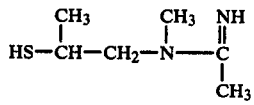
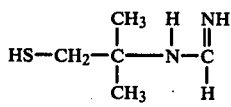
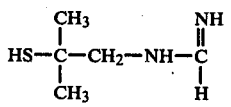
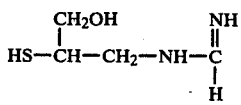
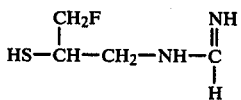
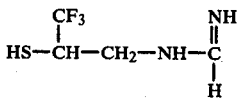
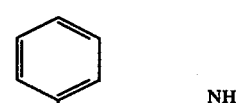
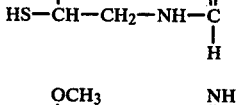
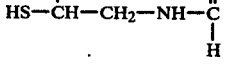

-continued
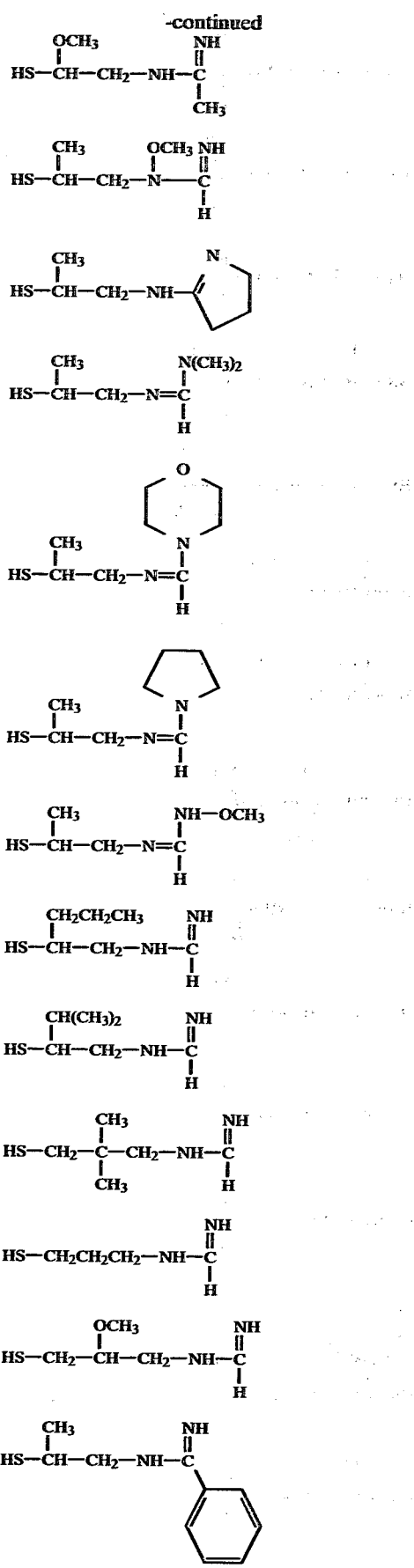
-continued
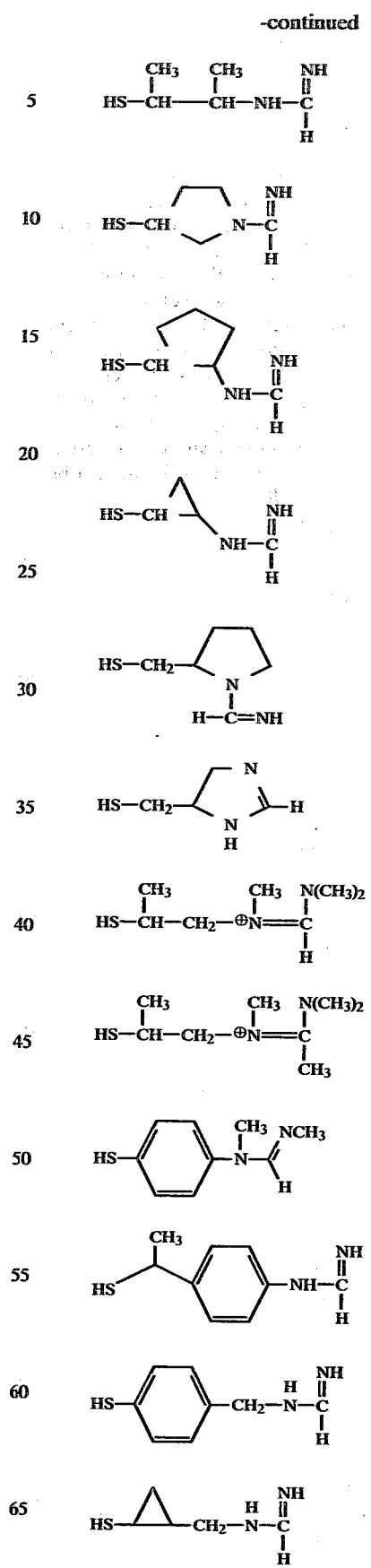

-continued

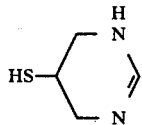

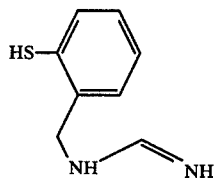

9. Guanidino and Guanidinium Mercaptans HSR$^8$: Wherein R$^8$ is:

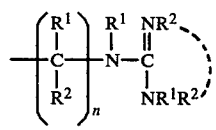

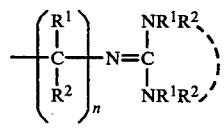

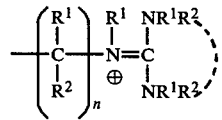

and wherein n=2-6; R$^1$ and R$^2$ are as initially defined under R$^8$; and the dotted line indicates provision for the ring formed by the joinder of substituents carried by the imino carbon atom. Such guanidino and guanidinium embodiments of the final products I are conveniently obtained by N-derivatization of the corresponding amino embodiments according to procedures disclosed in U.S. Pat. No. 4,194,047 as was explained under 8. above. Such guanidino embodiments are also conveniently prepared directly following the procedure described in co-pending, commonly assigned U.S. patent application Ser. No. 197,865 filed Oct. 17, 1980, which application is incorporated herein by reference. It should be noted that the cited application is directed to 1-carbadethiapenems, but that the disclosed process is useful by analogy. Representatively preferred values for R$^1$ and R$^2$ attached to the carbon atom include:
H,
CH$_3$,
CH$_2$CH$_3$,
CH$_2$OH,
OCH$_3$,
CH$_2$NH$_2$,
F,
phenyl,
CF$_3$,
CH(CH$_3$)$_2$,
CH$_2$CH$_2$CH$_3$,
CH$_2$F, benzyl, N(CH$_3$)$_2$
Representatively preferred values for R$^1$ and R$^2$ attached to nitrogen atoms include:
H,
CH$_3$,
CH$_2$CH$_3$,
CH$_2$CH$_2$OH,
—(CH$_2$)$_2$—
—(CH$_2$)$_3$—
CH(CH$_3$)$_2$
—(CH$_2$)$_4$—, phenyl, CH(CH$_3$)$_2$, C(CH$_3$)$_3$,
—CH$_2$CH$_2$OCH$_2$CH$_2$—
OCH$_3$, NH$_2$, NHCH$_3$, N(CH$_3$)$_2$ The following values for HSR$^8$ are also classified under the guanidino mercaptans, giving rise to the guanidino embodiments of I:
R$^8$ is:

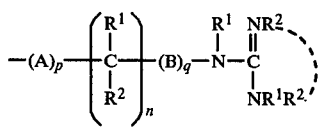

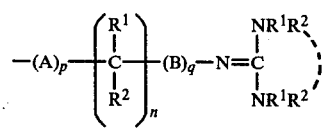

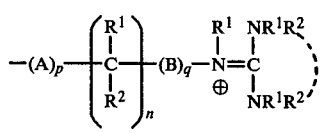

wherein R$^1$ and R$^2$ and n are as defined immediately above; p and q are 0 or 1; A and B are selected from: the aforementioned values for R$^8$ expressed in bivalent form from categories No.'s 1-7. Thus, A and B (or —R$^8$— are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); aryl aliphatic (see Class No. 5, above); heteroarylaliphatic, heterocyclylaliphatic, and heterocyclic (see Class No. 6, above); and alkyl-heteroatomalkyl (see Class No. 7, above); B is also selected from —O— and —NR'—.

EXAMPLES

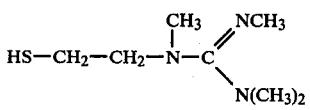

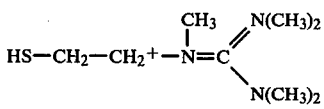

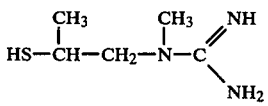

-continued

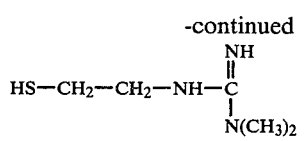
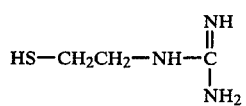
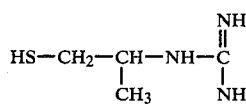
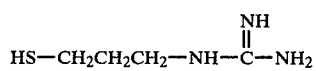
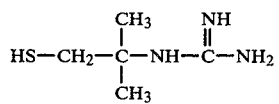
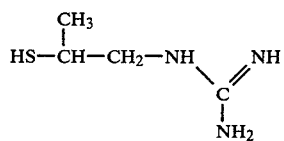
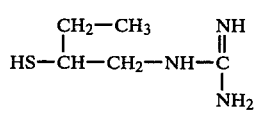
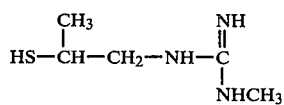
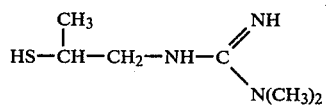
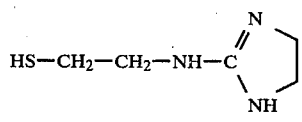
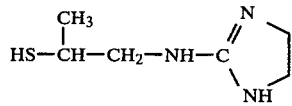
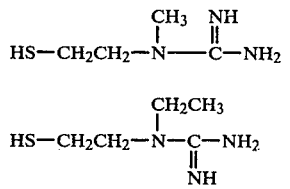
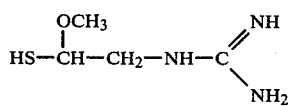

-continued

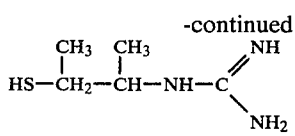
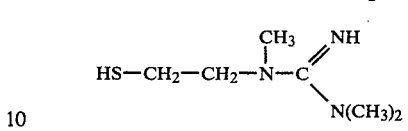
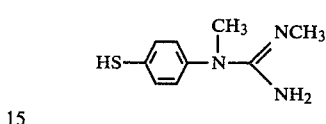
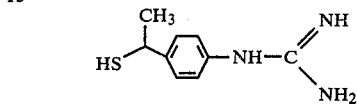
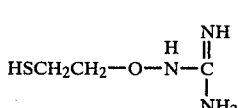
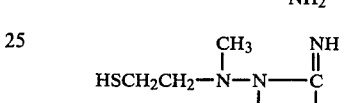
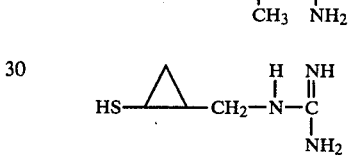

The compounds of the present invention (I) are valuable antibiotics active against various Gram-positive and Gram-negative bacteria and accordingly find utility in human and veterinary medicine. Representative pathogens which are sensitive to antibiotics I include: Straphylococcus aureus, Escherichia coli, Klebsiella pneumoniae, Bacillus subtilis, Salmonella typhosa Psuedomonas and Bacterium proteus. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy to inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of mens; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined 3-amido-6-substituted thio-1-azabicyclo [3.2.0] hept-6-en-2-one-7-carboxylic acid antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

Preparation of:

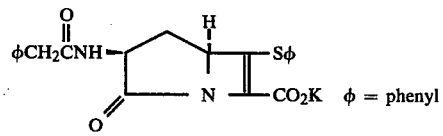

Step A:

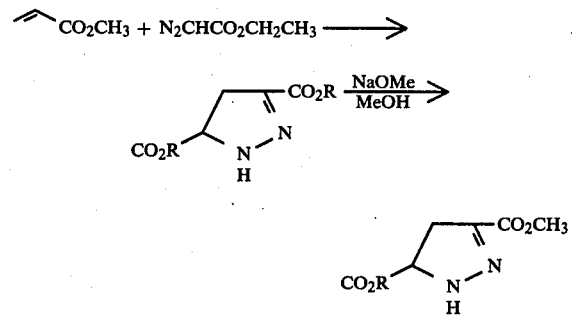

Methylacrylate (16.2 ml, 0.18 mole) was charged into a 100 ml RB flask equipped with a dropping funnel, thermometer and magnetic stirrer. Ethyldiazoacetate (20.0 g, 0.175 mole) was added dropwise with stirring and occasional cooling such that the temperature stayed in the range of 35°–45°. When the addition was complete the mixture was allowed to stand at room temperature for 36 hours. At the end of this period, the mixture was diluted with 300 ml dry methanol and 300 ml dry benzene, 0.5 g of sodium hydride added and the mixture distilled to a residual volume of 200 ml. This process was repeated with additional 300 ml portions of methanol and benzene at which point all of the ethyl ester had been converted to methyl ester. Dowex 50 (H+) (10 g) was added, the mixture stirred 20 min then filtered through an additional 10 g of Dowex 50 H+. The resin was washed with chloromethane and the combined organic filtrates were concentrated. The residue was taken up in 30 ml hot methanol, decolorized with charcoal and allowed to stand for crystallization. A first crop of 19.0 white crystalline pyrazoline was obtained.

Step B:

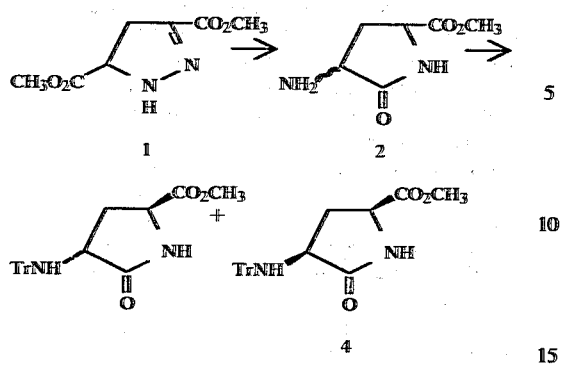

A solution of pyrazoline 1 (21.0 g, 0.113 mole) in 150 ml methanol and 100 ml tetrahydrofuran was treated with 3200 psi hydrogen at 110° in the presence of one teaspoon of Raney-Ni for 8 hrs. The catalyst was then removed by filtration and the filtrate evaporated in high vacuum to yield 2 as a blue foam. The crude amine 2 was dissolved in 400 ml dichloromethane and 16.8 ml (0.12 mole) of triethylamine and cooled to 0°. A solution of tritylchloride (31.5 g, 0.113 mole) in 150 ml tetrahydrofuran was added dropwise over 30 min with stirring. The mixture was allowed to stir at room temperature for 3 hrs at which point it was shown to be complete by tlc (silica gel 10:5:0.5 CHCl₃-ether-MeOH). The reaction was diluted with 300 ml of chloroform and 300 ml 10% aqueous potassium bicarbonate, the organic layer was separated, the aqueous layer was extracted with 100 ml CHCl₃ and the combined organics washed with brine, dried over Na₂SO₄ and evaporated to yield 45 g crude mixed trityl amines 3 as a blue foam. This crude product was dissolved in 50 ml warm dichloromethane, decolorized with charcoal and allowed to stand for crystallization. A crop of 18 g pure trans-isomer was obtained. Chromatography of the mother liquors on 200 g of silica gel with a 10–30% ethylacetatedichloromethane gradient afforded 14.5 g pure cis-isomer 4 as a white crystalline solid.

Step C:

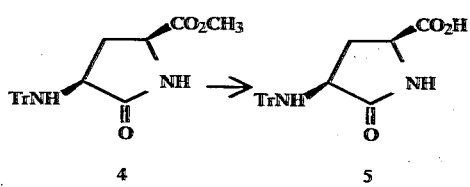

A solution of ester (4.0 g, 10 mmoles) in 100 ml tetrahydrofuran and 10 ml water was treated with 4.0 ml (2.5 N, 10 mmoles) aqueous sodium hydroxide and the resulting solution kept at room temperature for 3 hrs. The solvent was then evaporated and the residue partitioned between 100 ml dichloromethane and 30 ml water. The resulting gelatinous suspension was neutralized with 0.6 ml acetic acid with stirring, the organic layer was separated and the aqueous layer was extracted with 100 ml dichloromethane. The combined organics were washed with brine, dried over Na₂SO₄ and evaporated to yield crude acid. Crystallization from ether-dichloromethane afforded 3.4 g pure 5.

An exactly analogous hydrolysis of the trans-isomer (all amounts the same) produced 3.4 g of trans-acid.

Step D:

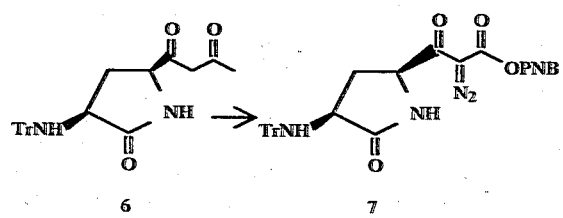

A solution of acid 5 (2.31 g, 5.98 mmoles) in 50 ml tetrahydrofurane was treated with 1.16 (7.18 mmoles) of 1,1-carbonyldiimidazole and the resulting solution stirred for 1 hour at room temperature. The magnesium salt of mono-p-nitrobenzylmalonic acid (3.0 g, 6.0 mmoles) was added, followed by 3.0 ml dry dimethylformamide. The resulting suspension was stirred at room temperature for 48 hours and then diluted with 100 ml of chloroform nd quenched with 30 ml of pH 4 phosphate buffer. The organic layers were separated and the aqueous phase was extracted with 2×100 ml chloroform. The combined organic phases were washed with brine, dried over sodium sulfate and evaporated to yield 4.5 g crude ketoester. Purification was effected by chromatography on 300 ml silica gel with a 10–20% ethylacetate-dichloromethane gradient as eluant to yield 1.93 g pure ketoester 6.

An exactly analogous procedure converted 3.40 g of trans-acid to 3.51 g trans-ketoester [THF 80 ml, CDI 1.71 g, DMF 8 ml, Mg salt 4.4 g]

Step E:

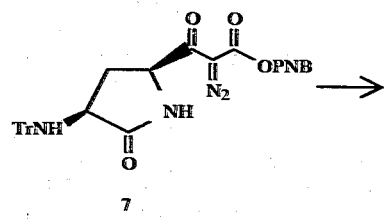

A solution of ketoester 6 (1.825 g, 3.24 mmoles) in 30 ml tetrahydrofuran and 20 ml acetonitrile was treated with 0.98 ml (7.0 mmoles) of triethylamine and 4.2 ml (0.8 M, 3.5 mmoles) of a hexane solution of p-dodecylbenzenesulfonyl azide. The resulting orange solution was stirred for 30 min and then concentrated and the residue chromatographed on 100 ml silica gel with a 10–20% ethylacetatedichloromethane gradient as eluant to yield 1.72 g pure diazo ketoester.

An exactly analogous procedure converted 3.50 g trans-ketoester to 3.45 g trans-diazo compound [30 ml 1:1 THF-CH₃CN, 2.1 ml triethylamine, 7.8 ml p-C₁₂H₂₅θSO₂N₃ soln.]

Step F:

-continued

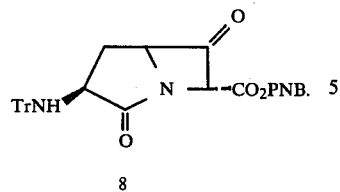
8

Diazoketoester 7 (496 mg, 0.842 mmole) was charged into a dry apparatus consisting of a 50 ml RB flask, condensor and magnetic stirrer. The apparatus was flushed with nitrogen and 5 ml dry dichloromethane and 2 mg rhodium (II) acetate were added. The mixture was refluxed for 1 hour at which point no starting material remained by tlc. The solvent was removed in vacuo with protection from atmospheric moisture and the resulting bicyclic ketoester used directly in the next step.

In an exactly analogous fashion 1.728 g trans-diazo was converted to bicyclic ketoester in 15 ml $CH_2Cl_2$.

Step G:

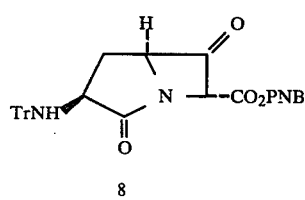
8

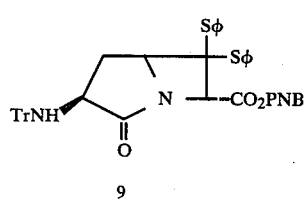
9

Bicyclic ketoester 8 (from 496 mg 7, 842 mmoles) was dissolved in 8.0 tetrahydrofuran and 10.0 ml acetonitrile and the solution cooled to −6°. 1,8-Diazabicyclo[5.4.- 0]undec-7-ene (0.127 ml, 0.85 mmole) was added, the mixture stirred 10 min at −60° followed by the addition of 0.176 (0.85 mmole) of diphenylchlorophosphate. The mixture was allowed to warm to −20° over 90 min to complete the formation of the end phosphate and then recooled to −70°. Benzenethiol (0.176 ml, 1.6 mmoles) and 0.278 ml (1.6 mmoles) of diisopropyl ethylamine were added and the mixture allowed to warm to room temperature over 90 min. The reaction was quenched with 10 ml pH 4 phosphate buffer, diluted with 80 ml $CHCl_3$ and subjected to the usual workup to yield a crude product which was purified by chromatography on 70 ml silica gel with 0–4% ether-dichloromethane gradient to yield 390 mg of 9.

In an exactly analogous fashion the trans-isomer of 8 (from 1.728 g of diazo ketoester) was converted to 1.30 g trans 9 [$CH_3CN$ 20 ml, THF 25 ml, DBU 0.45 ml, ($\theta O)_2POCl$ 0.621 ml, $\theta SH$ 0.660 ml, $iPr_2Net$ 1.04 ml]

In an exactly analogous fashion 750 mg of 8 was converted to 275 mg 9 ($R_8 = SCH_3$) [DBU 200 μl, ($\theta O)_2POCl$ 275 μl, $CH_3SH$ 0.25 ml, $iPr_2NEt$ 0.435 ml]

In an exactly analogous fashion 1.50 g of trans 8 was converted to 579 mg trans 9 ($R_8 = SMe$) [30 ml 1:1 THF-$CH_3CN$, DBU 417 μl, ($\theta O)_2POCl$, 579 μl, $CH_3SH$ 500 μl, $iPr_2NEt$ 750 μl]

Step H:

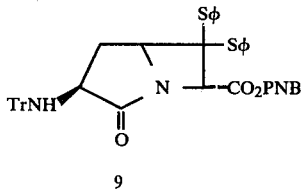
9

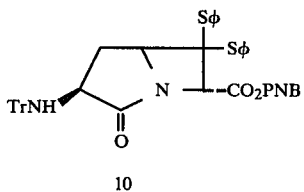
10

A solution of 384 mg (0.503 mmole) of 9 in 14 ml 1:1 methanol-tetrahydrofuran was treated wth 0.50 ml 1 M methanolic hydrochloric acid by dropwise addition. The resulting solution was allowed to stand one hour and then quenched with 0.060 ml of pyridine. The solvent was removed in vacuo (bath temp. 20°) and the residue dissolved in 10 ml dichloromethane and 0.060 ml triethylamine added. The solution was cooled to 0° and 0.075 ml of phenylacetyl chloride was added. The mxture was stirred at 0° for 30 min then quenched by the addition of 10 ml of 10% aqueous potassium bicarbonate. The usual aqueous workup followed by chromatography on 30 ml silica gel with a 6–15% ethylacetate-dichloromethane gradient afforded 228 mg of amide 10.

In an exactly analogous fashion trans-isomer of 9 (170 mg) afforded 85 mg of the trans-isomer of 10 [1 M HCl($CH_3OH$) 270 μl, py 60 μl, $\theta CH_2COCl$ 38 μl, triethylamine 60 μl.]

In an exactly analogous fashion 9 ($R_8 = SCH_3$) 275 mg was converted to 130 mg 10 ($R_8 = SCH_3$) [10 ml 1:1 THF-MeOH, 0.43 ml 1 M HCl (MeOH), pyridine 50 μl, $\theta CH_2COCl$ 63 μl, triethylamine 120 μl].

In an exactly analogous fashion trans 9 ($R_8 = SCH_3$) 579 mg was converted to 350 mg trans 10 ($R_8 = SCH_3$) [20 ml 1:1 THF-MeOH, 1.0 ml, 1 M HCl ($CH_3OH$), pyridine 100 μl, 140 μl, $\theta CH_2COCl$ and 200 μl triethylamine]

Step I:

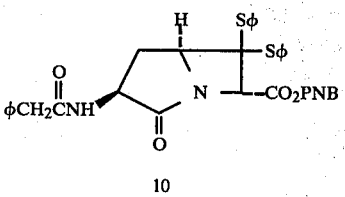
10

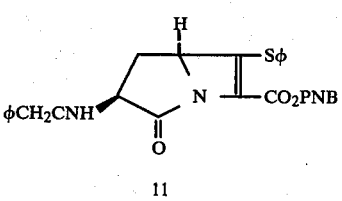
11

A solution of 210 mg (0.328 mole) of 10 in 5 ml dichloromethane was cooled to −10° and treated with a solution of 67 mg (0.33 mmole) of m-chloroperbenzoic acid in 2 ml of dichloromethane. After 5 min the reaction was complete by tlc so the mixture was diluted with 30 ml dichloromethane and washed with 10 ml 10% aqueous potassium bicarbonate containing a small amount of sodium sulfite. The organics were dried over sodium sulfate and evaporated to yield the crude sulfoxide, which was taken up in 5 ml dichloromethane, degassed with nitrogen and 150 μl diisopropylamine and 50 μl 1,8-diazabicyclo[5.4.0]-undec-7-ene added. The solution was stirred at 30° for 1 hour and then diluted with 30 ml dichloromethane and washed with 2×5 ml pH 4 phosphate buffer. The organic phase was dried over sodium sulfate, evaporated and the residue purified by chromatography on 15 ml silica gel with 10–20% ethylacetatedichloromethane gradient to yield 80 mg of olefin 11.

In an exactly analogous fashion the trans-isomer of 10 (530 mg) was converted to trans 11 (255 mg) [MCPBA 162 mg, $CH_2Cl_2$ 10 ml, DBU 119 μl, $iPr_2NH$ 224 μl]

In an exactly analogous fashion 10 ($R_8$=SMe), 100 mg, was converted to 40 mg of 11 ($R_8$=SMe) [MCPBA 41 mg, DBU 30 μl, $iPr_2NH$ 30 μl]

In an exactly analogous fashion trans 10 ($R_8$=SMe), 240 mg, was converted to 120 mg of trans 11 ($R_8$=SMe) [MCPBA 100 mg, DBU 75 μl, $iPr_2NH$ 140 μl]

Step J:

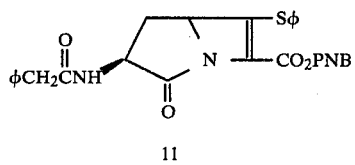

11

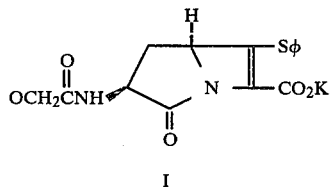

I

To a solution of 140 mg (0.261 mmole) of 11 in 15 ml of THF were added 3 ml of ethanol, 3 ml of water, 0.52 ml 1 M pH 7 phosphate bufer and 100 mg 10% palladium on charcoal. The miture was shaken under 50 psi of hdrogen for 1 hour and then diluted with 5 ml THF and 10 ml water and filtered through a 0.5 cm×2 cm column of charcoal with 5 ml water. The combined filtrate was adjusted to pH 7 with more buffer and then washed with 2×5 ml of ether. The aqueous phase was concentrated at 1 mm (bath temp. 20°) to remove ether and ethanol and then lyophilized to a volume of 10 ml. This solution was applied to three 0.5 mm Analtech reverse-phase tlc plates which were developed with 15% THF in water at 0°. The major uv active band was eluted with 40% aqueous acetonitrile, the eluate concentrated to one-half volume of 1 mm (bath temp. 20°), washed with 10 ml hexanes then lyophilized to a white powder which contained 88 μmoles of I by uv and nmr.

An exactly analogous deblock of the trans-isomer of 11 (all amouts the same) produced 105 μmoles of the trans-isomer of I.

An exactly analogous deblock of 11 ($R_8$=SMe), all amounts the same, produced 75 μmoles of I ($R_8$=SMe)

An exactly analogous deblock of trans 11 ($R_8$=SMe), 80 mg, produced 13.2 mg 36 μmoles of trans I ($R_8$=SMe). [THF 15 ml, $H_2O$ 4 ml, EtOH 4 ml, pH 7 buffer 0.4 ml Pd/C 80 mg]

EXAMPLE 2

Preparation of Pharmaceutical Compositions

One such unit dosage form is prepared by mixing 120 mg of compound A (the title compound of Example 1) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
| --- | --- |
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
| --- | --- |
| PARENTERAL SOLUTION Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound of the formula:

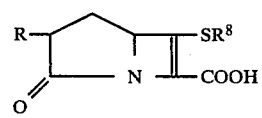

and the pharmaceutically acceptable salts and esters thereof, wherein R is $NHR^1$, $R^1$ is hydrogen, or acyl; wherein acyl is a radical of the formula:

wherein X is O or S and R" represents hydrogen; amino; alkylamino or dialkylamino wherein the alkyl radical comprises 1 to 6 carbon atoms; substituted or unsubstituted; straight or branched chain alkyl wherein the alkyl radical comprises 1 to 6 carbon atoms; alkylthio comprising 1 to 6 carbon atoms; phenylthio comprising 6 to 10 carbon atoms; hydroxy; alkoxy comprising 1 to 6 carbon atoms; phenyloxy; alkenyl, or alkynyl groups comprising 2 to 6 carbon atoms; phenyl; benzyl; cycloalkyl comprising 3 to 6 carbon atoms; or a heteroaryl or heteroaralkyl group (mono- and bicyclic) wherein the alkyl moiety comprises 1 to 3 carbon atoms and the heterocyclic ring comprises 4–10 atoms consisting of 1–6 carbon atoms and 1–4 heteroatoms and the heteroatoms are selected from O, N and S; such above-listed groups can be unsubstituted or can be substituted by radicals such as OH, SH, SR° (R° is lower alkyl or phenyl), alkyl or alkoxy groups having 1 to 6 carbon atoms, chloro, bromo, fluoro, iodo, cyano, carboxy, sulfamino, carbamoyl, sulfonyl, azido, amino, alkylamino including quaternary ammonium wherein the alkyl group comprises 1 to 6 carbon atoms, trifluoromethyl, carboxyalkyl, carbamoylalkyl, N-carbamoylalkyl, wherein the alkyl moiety of the foregoing four radicals comprises 1 to 6 carbon atoms, amidino, guanidino, N-substituted guanidino, guanidino lower alkyl; or the acyl group is a radical of the formula:

wherein X is O or S and n is 0–4, Z represents oxygen, sulfur, carbonyl or nitrogen and R" is defined as above; or the acyl group is a radical of the formula:

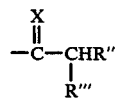

wherein R" is defined as above and R''' is a radical selected from the group consisting of amino, hydroxy, azido, carbamoyl, guanidino, amidino, acyloxy, Cl, F, Br, I, sulfamino, tetrazolyl, sulfo, carboxy, carbalkoxy, and phosphono or if X is oxygen, the acyl group may also be a radical of the formula:

wherein $R^3$ represents hydrogen, chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl, substituted heterocycle, heterocyclic thio, or substituted heterocyclic thio containing one or more oxygen, sulfur or nitrogen atoms in the ring, phenylthio, phenyloxy, lower alkyl of 1–6 carbon atoms, or cyano, wherein the substituents on the moieties $R^3$ and $R^4$, can be halo, carboxymethyl, guanidino, guanidinomethyl, carboxamidomethyl, aminoethyl, nitro, methoxy or methyl; and $R^8$ is independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; phenyl; phenylalkyl, phenylalkenyl, and phenylalkynyl wherein the aliphatic portion has 1–6 carbon atoms; heteroaryl, heteroaralkyl, heterocyclyl and heterocyclylalkyl, wherein the heteroatom or atoms are selected from 1–4 O, S, N and wherein the alkyl moieties associated with said heterocyclic moieties have 1–6 carbon atoms; wherein the substituent or substituents relative to the above-named radical $R^8$ are selected from the group consisting of:

—X° halo (chloro, bromo, fluoro)

—OH hydroxy

—$OR^1$ alkoxy, phenyloxy

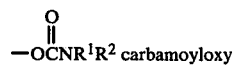

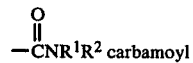

—$NR^1R^2$ amino

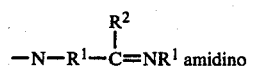

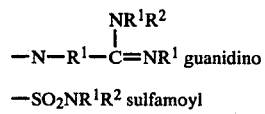

—$SO_2NR^1R^2$ sulfamoyl

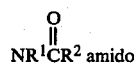

—$CO_2H$ carboxy

—$OSO_3R^1$ sulphate

—$NO_2$ nitro

—$\overset{+}{N}(R^1)_3$ ammonium ($R^1$ groups independently chosen)

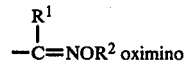

—$CO_2R^1$ carboxylate

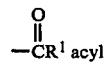

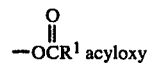

—SH mercapto

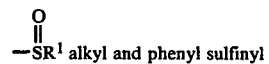

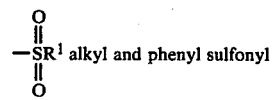

-continued

—CN cyano

—N₃ azido

—SR¹ alkyl- and phenylthio

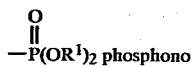
—P(OR¹)₂ phosphono

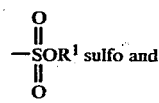
—SOR¹ sulfo and

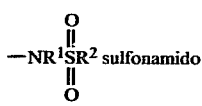
—NR¹SR² sulfonamido wherein, relative to the above listed substituents on R⁶, R⁷, and R⁸, the groups R¹ and R² are independently selected from: hydrogen, alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; phenyl; phenylalkyl, phenylalkenyl, and phenylalkynyl wherein the aliphatic portion has 1-6 carbon atoms; heteroalkyl, heteroaralkyl, heterocyclyl and heterocyclylalkyl and wherein the heteroatom or atoms in the above-named heterocyclic moieties are selected from the group consisting of 1-4 oxygen, nitrogen or sulphur atoms and wherein the alkyl moieties associated with said heterocyclic moieties have 1-6 carbon atoms; additionally R⁸ substituents are selected from the group consisting of

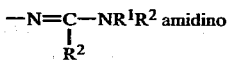
amidino

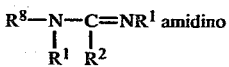
amidino

—N—C=ṄR¹R² amidinium
 |   |
 R¹  R²

—N=C—NR¹R² guanidino
    |
    NR¹R²

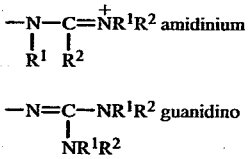
guanidino

—N—C=ṄR¹R² guanidinium.
 |   |
 R¹  NR¹R²

2. A compound according to claim 1 wherein R⁸ is CH₂CH₂NH₂.

3. An antibiotic method of treatment comprising administering a therapeutically effective amount of a compound according to claim 1.

4. An antibiotic pharmaceutical composition comprising a therapeutically effective amount of a compound according to claim 1 and a carrier therefor.

* * * * *